United States Patent [19]

Larson et al.

[11] Patent Number: 4,522,793

[45] Date of Patent: Jun. 11, 1985

[54] REMOVING H₂S FROM NATURAL GAS USING TWO-STAGE MOLECULAR SIEVES

[75] Inventors: Harold A. Larson; Manfred F. Boehme; Jeffrey W. Sheets, all of Bartlesville, Okla.

[73] Assignee: Phillips Petroleum Company, Bartlesville, Okla.

[21] Appl. No.: 508,710

[22] Filed: Jun. 28, 1983

[51] Int. Cl.³ .......................... C01B 17/00; B01J 1/00
[52] U.S. Cl. .................................... 423/230; 423/244; 423/416
[58] Field of Search ........... 423/220, 230, 245, 244 R, 423/416

[56] References Cited

U.S. PATENT DOCUMENTS

| | | | |
|---|---|---|---|
| 2,809,097 | 10/1957 | Adcock et al. | 423/416 |
| 3,078,634 | 2/1963 | Milton | 55/33 |
| 3,144,307 | 8/1964 | Haines, Jr. | 23/225 |
| 3,186,789 | 6/1965 | Ward et al. | 23/3 |
| 3,363,401 | 1/1968 | Pierre et al. | 55/73 |
| 3,409,399 | 11/1968 | Bertozzi et al. | 423/416 |
| 3,620,969 | 11/1971 | Turnock et al. | 208/245 |
| 3,864,452 | 2/1975 | Chi et al. | 423/244 |

FOREIGN PATENT DOCUMENTS

| | | | |
|---|---|---|---|
| 1196624 | 7/1965 | Fed. Rep. of Germany | 423/416 |
| 80797 | 3/1971 | German Democratic Rep. | 423/230 |
| 885871 | 12/1961 | United Kingdom | 423/416 |
| 955724 | 4/1964 | United Kingdom | 423/244 R |

Primary Examiner—L. Dewayne Rutledge
Assistant Examiner—Christopher W. Brody

[57] ABSTRACT

An integrated process for removal of hydrogen sulfide and water from a natural gas stream by contacting a natural gas stream containing hydrogen sulfide, water, and $CO_2$ with molecular sieves that act both as an adsorbent for hydrogen sulfide and water and as a catalyst for the reaction for conversion of hydrogen sulfide and carbon dioxide to carbonyl sulfide. About 92 to about 95 volume percent of an inlet natural gas stream is passed into contact with molecular sieves to produce a salable gas. A portion of this salable gas is used as regeneration fluid for the molecular sieve contactors and the regeneration gas effluent from the regeneration process is diluted with the remainder of the inlet gas stream and subjected to further adsorption/conversion contact with molecular sieves to produce salable gas that is mixed with the first treated gas stream. Depending upon the degree of compression of the regeneration gas effluent from the regeneration operation, the integrated system can be operated with two phases of adsorption or with a single phase of adsorption of mixed streams of inlet gas and regeneration gas.

6 Claims, 4 Drawing Figures

REMOVING H₂S FROM NATURAL GAS USING TWO-STAGE MOLECULAR SIEVES

BACKGROUND OF THE INVENTION

This invention relates to the removal of impurities from natural gas. In one of its aspects this invention relates to the removal of hydrogen sulfide as an impurity from a stream of gas. In another of its aspects this invention relates to adsorption using molecular sieves. In still another aspect of this invention it relates to the conversion of hydrogen sulfide to carbonyl sulfide (COS) in the presence of a molecular sieve catalyst.

Perhaps the best known and most frequently used means for removing hydrogen sulfide contaminant from a gas stream, particularly a natural gas stream, is the use of an amine contactor for the absorption of the H₂S. This system is not, however, economically attractive for the selective absorption of H₂S when the ratio of carbon dioxide to hydrogen sulfide is high. In such a system it is necessary to remove the majority of the CO₂ to insure adequate removal of the H₂S. In a standard amine absorbant system the majority of the energy used to run an amine contactor, an amine regeneration system, and a waste gas incinerator is used to remove CO₂.

As another type of economically attractive system for the removal of H₂S contaminant, molecular sieves can be used to remove H₂S by a combination of adsorption and chemical conversion of H₂S to carbonyl sulfide (COS). In such a system, the regeneration of the molecular sieve bed causes the concentration of the H₂S in the regeneration gas stream to be much higher than in the original gas stream. The removal of H₂S and water from the molecular sieve bed regeneration gas which normally is accomplished using an amine contactor followed by a glycol contactor has been shown not to be economically attractive if, as stated above, the ratio of CO₂ to H₂S is high.

In solving the problem of providing an adsorption and regeneration system for removal of hydrogen sulfide contaminant from gases, particularly natural gas, it has now been found that an integrated system using molecular sieve beds can be used to eliminate the need for an amine absorption system and the glycol dehydration system that is normally used in conjunction with the amine system.

It is therefore an object of this invention to provide a process for the removal of hydrogen sulfide contaminant from a gas stream using contact with molecular sieves both to treat an inlet gas stream to remove sufficient hydrogen sulfide and water to produce a salable effluent and to treat the effluent from the regeneration of the molecular sieves so that a salable product is produced from this stream. It is also an object of this invention to provide a method for producing natural gas of reduced hydrogen sulfide content and a water dew point of less than −70° C.

These and other objects, aspects, and the various advantages of this invention will become apparent upon study of the specification, the drawing, and the appended claims.

STATEMENT OF THE INVENTION

In accordance with this invention, an integrated process is provided for removal of hydrogen sulfide and water from natural gas in which a natural gas stream containing hydrogen sulfide and water is contacted with molecular sieves which act both as (1) an adsorbant for hydrogen sulfide and water and (2) catalyst in the reaction for conversion of hydrogen sulfide and carbon dioxide to carbonyl sulfide and H₂O. In this process about 92 to about 95 volume percent of the natural gas stream is contacted with molecular sieves in a first phase of contactors to produce, by adsorption and conversion of H₂S to COS, a first treated gas stream of sufficiently low H₂S and H₂O content to be salable. A portion of this first treated gas stream is heated and passed back through the molecular sieve bed of the first phase of contactors as regeneration gas to desorb that adsorbed H₂S so that a first low pressure regeneration gas stream is produced. The first low pressure regeneration gas stream (first stage) and a second low pressure regeneration gas stream (second stage) and the remainder of the inlet stream are then further treated to provide a second treated gas stream from which at least a portion of water and heavy liquid hydrocarbons have been removed and this treated gas stream contacted with molecular sieves to produce, by adsorption and conversion of H₂S to COS, a second treated gas stream of sufficiently low H₂S and H₂O content to be mixed with the first treated gas stream with the salable quality of the mixture being retained.

In a first embodiment of the invention a natural gas stream is contacted with molecular sieves in a first stage of contactors in which the sieves act both as (1) an adsorbant for hydrogen sulfide and water and (2) as a catalyst in the reaction for conversion of hydrogen sulfide and carbon dioxide to carbonyl sulfide. In the process of this embodiment the inlet gas stream containing hydrogen sulfide and carbon dioxide contaminants is divided into three streams with most of the inlet stream, up to 95 volume percent, being passed immediately into contact with molecular sieves to produce by adsorption and conversion of H₂S to COS an effluent stream of sufficiently lowered H₂S content to be salable but with a portion of this effluent gas being passed as regeneration gas through the molecular sieve beds to desorb the adsorbed H₂S thereby producing a low pressure regeneration gas. A second portion of the inlet gas is used to regenerate the second stage adsorbers thereby producing a low pressure regeneration gas having a higher average hydrogen sulfide content than the low pressure regeneration gas produced in regenerating the first stage molecular sieves. The two low pressure regeneration gas streams are joined and passed through cooling means of sufficiently low temperature to condense heavy liquid hydrocarbons and water which are removed from the stream which is then combined with the remainder of the inlet gas which has been heated to a compatible temperature and which is used to dilute the H₂S content of the low pressure regeneration streams. The diluted regeneration gas is then scrubbed contacted with molecular sieves in the second stage of contactors thereby producing by adsorption and reaction of H₂S to COS a stream of equally low H₂S content as compared to the effluent of the first stage of contactors, but of elevated, although sufficiently low COS content, to be combined with the effluent from the first stage to provide salable product.

In another embodiment of the invention, the addition of a step in which the low pressure regeneration gas is subjected to compression to a pressure that is in a range below that at which the inlet natural gas enters the system allows for additional versatility in operation by reducing the amount of equipment necessary to carry out the contacting of treated regeneration gas with molecular sieves. In this embodiment, as in the embodiment described above, a natural gas stream is contacted with molecular sieves in a first stage of contactors in which the sieves act both as (1) an absorbant for hydrogen sulfide and water and (2) as a catalyst in the reaction for conversion of hydrogen sulfide and carbon dioxide to carbonyl sulfide and water. The inlet gas stream containing hydrogen sulfide and carbon dioxide contaminants is divided into two streams with up to about 95 volume percent being passed immediately into contact with molecular sieves in a first phase of contactors to produce by adsorption and conversion of $H_2S$ to COS an effluent stream of sufficiently low $H_2S$ content to be salable but with a portion of this effluent gas being passed as regeneration gas through the molecular sieve beds to desorb the adsorbed $H_2S$ thereby producing a low pressure regeneration gas. This low pressure regeneration gas and a stream of regeneration gas produced from the second phase contactors, as will be described below, are subjected to cooling to condense heavy hydrocarbons and water which are removed and the gas is then passed to a compression step in which the pressure of the regeneration gas stream is raised to a range below that of the inlet natural gas and is then combined with the remainder of the inlet natural gas to produce a diluted regeneration gas stream which is subjected to scrubbing. The scrubbed, diluted regeneration gas is then passed into contact with molecular sieves in the second phase of contactors thereby producing by adsorption and reaction of $H_2S$ to COS a stream of equally low $H_2S$ content as compared to the effluent of the first stage of contactors, but of elevated, although sufficiently low COS content, to be combined with the effluent of the first stage to provide salable product. A portion of the treated second phase effluent is passed back through the molecular sieve beds of the second phase as regeneration gas thereby producing a second low pressure regeneration gas stream which is recycled in the system as described above.

In a third embodiment of the invention the compression of the low pressure regeneration gas brings the regeneration gas to the same pressure as the inlet natural gas stream thereby eliminating the necessity for having a second phase of molecular sieve treatment. In this embodiment from about 92 to about 95 volume percent of the inlet gas stream containing hydrogen sulfide, water and carbon dioxide contaminants is passed immediately into contact with molecular sieves to produce by adsorption and conversion of $H_2S$ to COS an effluent stream of sufficiently low $H_2S$ and water content to be salable, but with a portion of this effluent gas being passed as regeneration gas through the molecular sieve beds to desorb the adsorbed $H_2S$ thereby producing a low pressure regeneration gas. This low pressure regeneration gas is subjected to cooling to condense hydrocarbons and water which are removed from the system and the low pressure regeneration gas is then subjected to compression to bring the pressure of the regeneration gas up to a pressure equal to that of the inlet natural gas. The remainder of the inlet natural gas stream and the effluent from the compression step are combined to produce a diluted, regeneration gas which is subjected to scrubbing. The scrubbed, diluted regeneration gas stream is then divided into equal portions and passed along with the 92 to 95 percent by volume of inlet natural gas through the molecular sieve contactors so that once flow is established in the system each molecular sieve contactor has as inlet an amount of inlet natural gas and an amount of the scrubbed, diluted regeneration gas that is about the same fractional portion of the total flow of each of these streams.

It can be seen that the embodiment of this invention using the least additional energy consumption requires the greatest investment in contact equipment and the most complicated use of this equipment. By increasing the pressure of the regeneration gas stream, the use of two different treatment streams for contacting the diluted regeneration gas with the molecular sieves can be eliminated.

As can be seen from the general statement of the process and the embodiments above, and as will be more particularly pointed out in the illustrative descriptions below, the inventive concept lies in the division of the inlet stream for handling molecular sieve contact so that treated gas can be used as regeneration gas for the sieves and then further treated to remove water and additional $H_2S$ by recombination of the streams to provide efficient contacting with molecular sieves thereby eliminating the use of other costly adsorbant systems.

"Molecular sieves" useful in the process of this invention are chosen from both natural and synthetic solid adsorbants which are porous solids having voids of pore spaces having voids of dimensions that will effectively sieve from the gas stream only those molecules of a size small enough to enter the pores with all other molecules of larger size being rejected by the adsorbant. The extracted molecules, adsorbed on the walls of the pores, can be desorbed therefrom using a suitable desorbing means. By selecting a suitable molecular sieve hydrogen sulfide molecules may be effectively sieved from a stream of hydrocarbon gases containing the hydrogen sulfide.

It has also been found that certain molecular sieves act as a catalyst for the conversion of hydrogen sulfide and carbon dioxide to carbonyl sulfide. It is this characteristic, particularly, which enables the use of molecular sieve beds without other adsorbing means in the process of this invention. For this invention, any molecular sieve can be used that is of pore size selectively to adsorb hydrogen sulfide and which will act as a catalyst for the production of carbonyl sulfide. The molecular sieves particularly useful in this invention are Type 4A molecular sieves—the sodium zeolite A with apparent pore size of 4 angstrom units, which are readily available commercially.

The process of this invention can best be understood in conjunction with the drawing in which.

Figure 1:
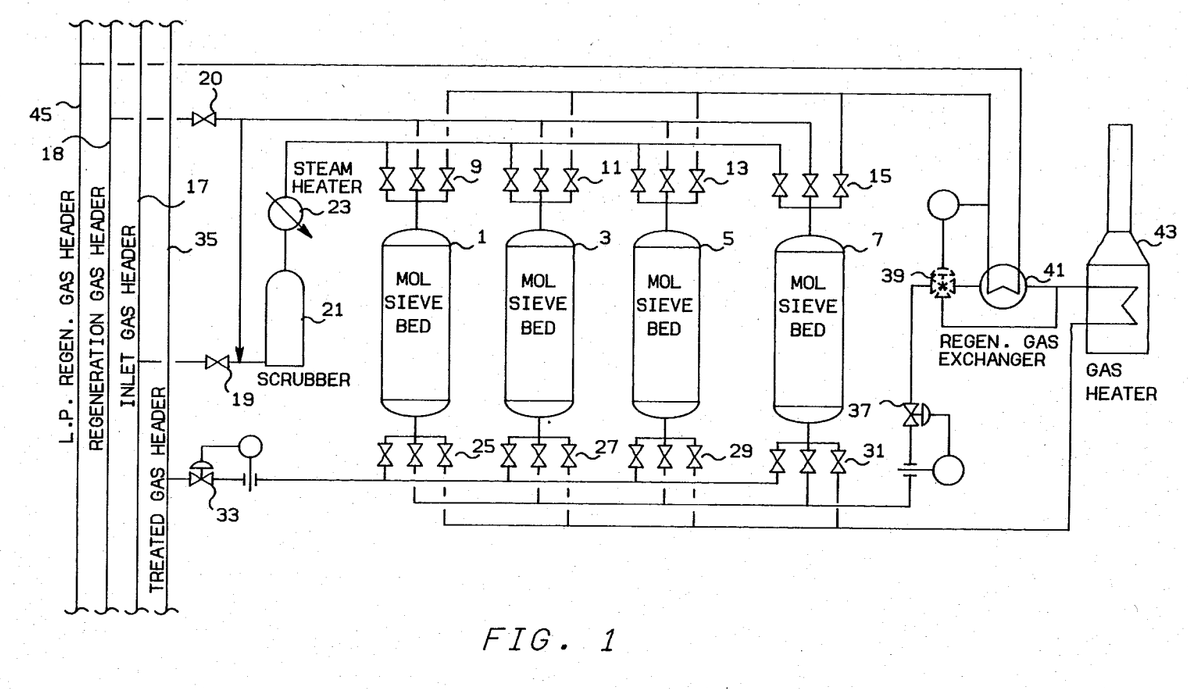
FIG. 1 shows a standard arrangement of a train of molecular sieve beds with regeneration equipment.

Referring now to FIG. 1, the apparatus used in a typical molecular sieve contact system is set up in what is usually referred to as a train which includes the molecular sieve beds, the regeneration gas heating system, condensate removal containers, and the attendant piping and control system. Typically, a set of four molecular sieve beds (1) (3) (5) (7) are arranged with multiple valving systems (9) (11) (13) (15) so that inlet gas from header (17) can be directed through valve (19) or the gas from the regeneration gas header (18) can be directed through valve (20) through the scrubber (21) and heater (23) into each or all of the molecular sieve beds. Similarly, multiple valving system (valve trees) (25) (27) (29) (31) are arranged on the outlet piping of the sieve beds so that effluent can be directed through a control valve (33) into a treated gas header (35) or a slip stream through control valves (37) (39) into heat exchanger (41) and gas heater (43) to be returned through a valve in the same valve tree (25) (27) (29) (31) into a molecular sieve bed as regeneration gas. The regeneration gas passing upward through the bed can be exited through a valve on the valve tree (9) (11) (13) (15) through the tube side of heat exchanger (41) and thence to a sour, or low pressure, regeneration gas header (45). In operation all valves in the valve tree are closed except that one through which gas is flowing. In a first stage contact bed train, one of the beds will be in regeneration while the other three beds are processing inlet gas. In the second stage, one train with two beds always in service treats a diluted regeneration gas stream while a second train always has one bed in regeneration.

Figure 2:
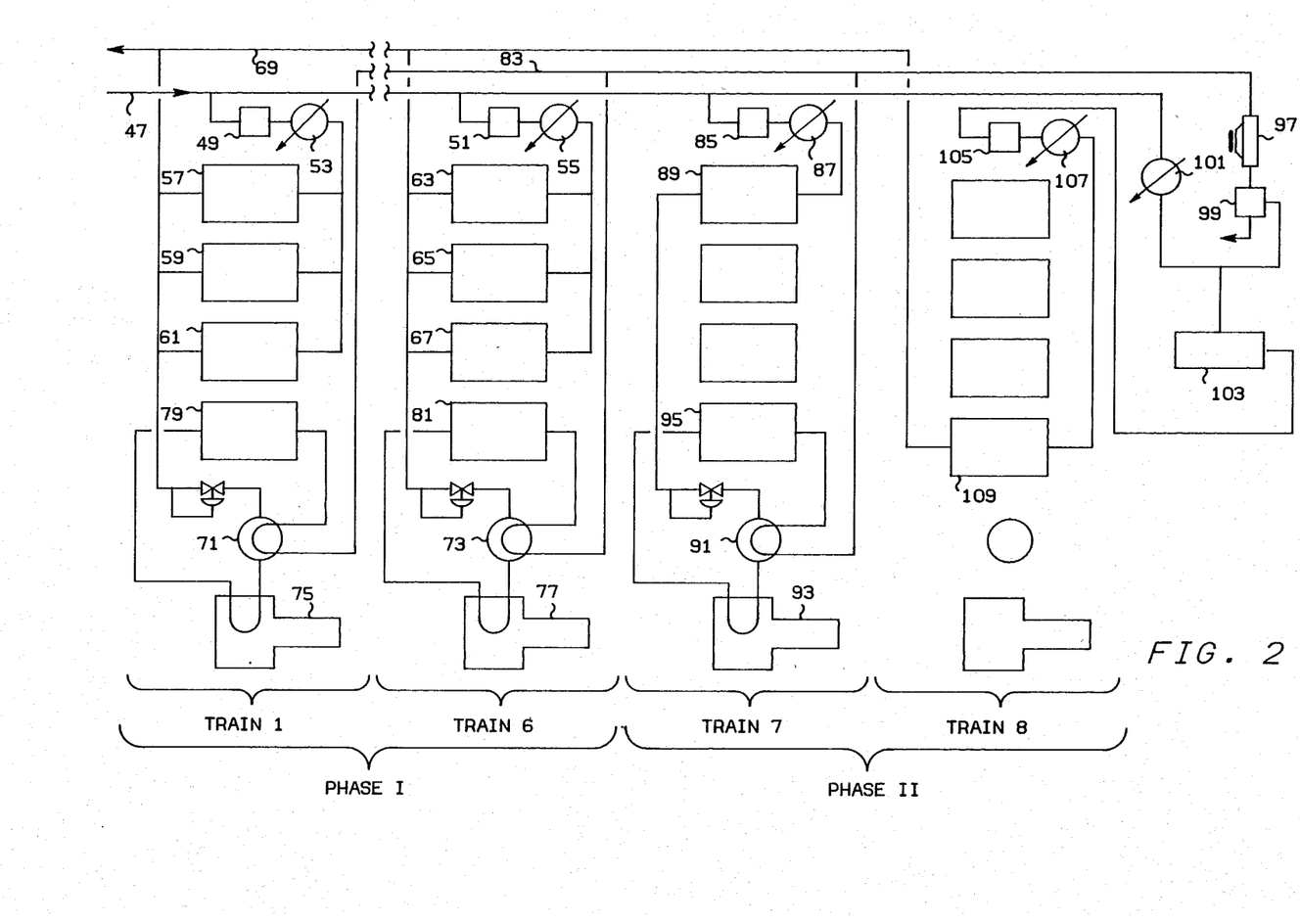
FIG. 2 shows a typical operating configuration of molecular sieve beds for the process of this invention using two phases of adsorption without compression.

Referring now to FIG. 2, serving as an example of the process, a typical operation of the present invention will be described for removal of hydrogen sulfide by the process of this invention from an inlet natural gas having an average hydrogen sulfide content of about 12.7 mg sulfur per $Nm^3$ which, carbon dioxide present in an amount to at least react stoichemetrically with the $H_2S$ to produce COS and for the purposes of this illustration having an inlet volume of $32 \times 10^6$ $Nm^3/D$.

In FIG. 2 each of the contact trains contains the items of equipment, piping, and valving as shown in FIG. 1, but all piping and valving not in service has been eliminated from the present figure for the sake of simplification. For the purpose of this example the molecular sieve beds containing Type 4A molecular sieves are sized to accommodate a flow volume of up to 90,000 $Nm^3/hr$ in the individual contactors of phase II while the average flow volume for each of the contactors of phase I is less than 150,000 $Nm^3/hr$. The $32 \times 10^6$ $Nm^3/D$ inlet volume for this example dictates the use of three trains in phase I. Again for the purpose of simplification only two of these trains are shown in FIG. 2.

$29.31 \times 10^6$ $Nm^3/D$ of natural gas containing an average of about 12.7 mg of sulfur/$Nm^3$ in the form of hydrogen sulfide is passed through line 47 to be divided between three trains of phase 1 where an inlet volume of about 407,000 $Nm^3/hr$ per train. This inlet flow passes through scrubbers (49) (51) and heat exchangers (53) (55) to raise the inlet temperature in the contactors (57) (59) (61) (63) (65) (67) to a range of about 5° to about 15° C., preferably about 10° C.

In the contactors the hydrogen sulfide in the inlet gas is partially adsorbed onto the molecular sieves—about 42 percent—and partially reacted into COS—about 58 percent—so that the treated gas effluent from the contactors has a hydrogen sulfide content of about 1 milligram of sulfur/$Nm^3$ and a COS content of about 7.4 milligram sulfur/$Nm^3$. This material is of salable sulfur content and also has a sufficiently low dew point, preferably less than −70° C., so that the majority of the effluent is passed into the treated gas header 69.

About 22,000 $Nm^3/hr$ of treated gas is diverted from each of the first phase trains through a heat exchanger (71) (73) and a heating furnace (75) (77) to raise the temperature of the effluent gas to about 290° C. This hot gas is then passed as regeneration gas in a flow counter to the adsorption flow through contactors (79) (81) for a period sufficient to regenerate the contactor bed. During the heating phase of this regeneration about 61% of the $H_2S$ adsorbed on the molecular sieves is converted to COS (experience shows that extended heating improves the conversion). The effluent regeneration gas averages hydrogen sulfide in an amount of about 32.3 milligrams of sulfur/$Nm^3$ and COS in an amount of about 57.6 milligrams of sulfur/$Nm^3$. This regeneration gas passes through the tube side of heat exchanger (71) (73) to the low pressure regeneration gas header (83).

It can be seen from the discussion above that the purpose of phase I is to treat about 95% of the inlet volume of the gas to produce a product with a salably acceptable hydrogen sulfide and COS content using a small portion of this treated gas to provide regeneration gas for the molecular sieve contactors in each of the trains For the purposes of this example, about 22,000 $Nm^3/hr$ of inlet gas is passed from the inlet gas header (47) through scrubbers (85), heat exchanger (87) through contactor (89) through heat exchanger (91), gas heater (93) and as regeneration gas to contactor (95). The desorbing of contactor (95) produces an effluent having an average $H_2S$ content of about 56.6 milligrams of sulfur/$Nm^3$ and a COS content of about 69.8 milligrams of sulfur/$Nm^3$. This effluent is passed through the tube side of heat exchanger (91) and into the low pressure regeneration gas header (83).

The effluent in the low pressure regeneration gas header (83) is passed through a cooler (97) and a condensate collection pot (99) from which water and heavy liquid hydrocarbons are drained. The low pressure regeneration gas is then combined with about 90,000 $Nm^3/hr$ of inlet gas that has been passed through a heater (101) that raises temperature from about 5° C. to about 15° C. This inlet gas is used to dilute the amount of hydrogen sulfide in the regeneration gas in the low pressure regeneration gas header. The combined stream then passes through scrubbers (103) and (105) for removal of heavy hydrocarbons and then through heater (107) which is normally not in service as no heating is required here.

The effluent from contactors (109) and (111) about 180,000 $Nm^3/hr$ has a hydrogen sulfide content of about 1 milligram of sulfur/$Nm^3$, a dew point of less than −70° C., and a COS content of about 40.3 milligrams of sulfur/$Nm^3$. This effluent is passed into the treated gas header (69) where it is mixed with and diluted by treated gas from phase I to produce a sales gas having a hydrogen sulfide content of about 1 milligram of sulfur/$Nm^3$ and a COS content of about 11.8 milligrams of sulfur/$Nm^3$ providing an overall $H_2S$ conversion of 92 to 93 percent.

It is important to note the cycling of the individual contactors in the molecular sieve trains between adsorption and regeneration cycles which allows the integrated process of this particular embodiment to be successfully operated. Referring both to FIG. 1 and FIG. 2, it can be seen that in each of the adsorption trains of phase I, the individual valves in the valve trees (9), (11), (13), (15), (25), (27), (29), (31) can be set so that natural gas can be admitted from the inlet gas header into molecular sieve beds (1), (3), (5) of FIG. 1 which correspond to sieve beds (57), (59), (61) of FIG. 2 with the outlet gas returning to the treated gas header, but with one valve set in an outlet valve tree, for example (29) to admit flow through valve (37) and the regeneration gas heating system for back flow through molecular sieve bed (7) to regenerate this sieve bed. The obvious cycle allows regeneration of sieve bed (7) for one quarter of any given cycle period, for instance, 12 hours out of a 48 hour total cycle so that after a 12 hour regeneration, sieve bed (7) is returned to adsorption service and sieve bed (1) begins a 12 hour regeneration period. With each sieve bed taken in turn for regeneration, in full cycle an individual sieve bed would be in adsorption service for 36 hours and then be regenerated for 12 hours.

The adsorption trains of phase II, however, must be handled for regeneration in a cycle that involves two trains. Relating the scheme of FIG. 2 to an individual train diagram of FIG. 1, it can be seen that while sieve beds (109) and (111) of train 8 are in adsorption service treating the scrubbed, diluted regeneration gas stream, sieve bed (95) of train 7 is in regeneration service. In train 7 by seriatim cycling in which a sieve bed is used for regeneration for 12 hours, it can be seen that at the end of 48 hours a train consisting of four sieve beds is in the state in which all four beds were regenerated and ready for adsorption service. During this same 48 hour period, each of the four sieve beds in train 8 has been placed seriatim in adsorption service for 24 hours (always two beds in service) so that at the end of 48 hours there are four molecular sieve beds that need regeneration. The valves at the inlet header can then be switched so that the molecular sieve vessels of train 7 can be used seriatim for adsorption of the diluted regeneration gas and the molecular sieve beds of train 8 can be regenerated.

Figure 3:
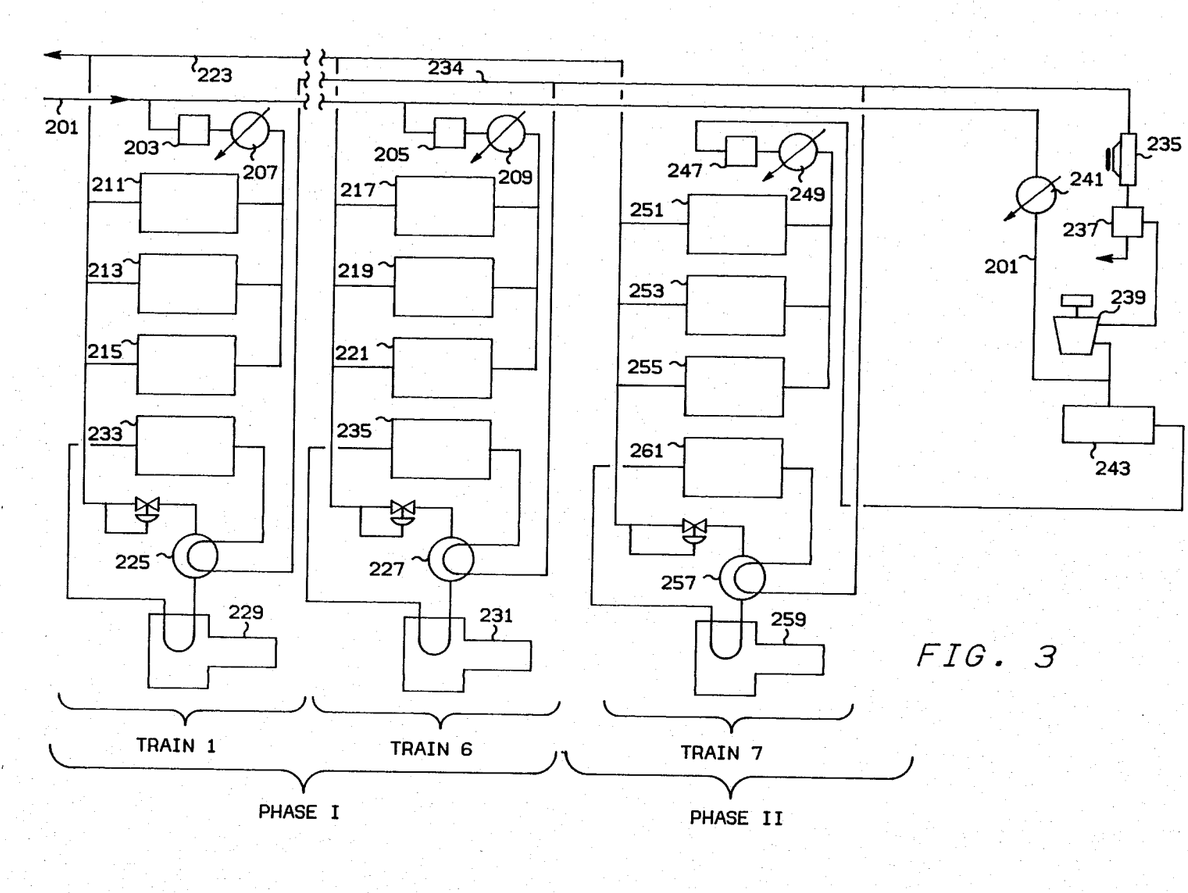
FIG. 3 shows a typical operating configuration of molecular sieve beds for the process of this invention using two phases of adsorption and compression.

Referring now to FIG. 3, a typical operation of the present invention using two phases of adsorption with compression of the regeneration gas stream will be exemplified. As in the previous exemplification, each of the contact trains contains the items of equipment, piping, and valving as shown in FIG. 1, but all piping and valving not in service have been eliminated from the present figure for the sake of simplification.

Inlet natural gas containing an average of about 12.7 mg of sulfur/$Nm^3$ in the form of hydrogen sulfide is passed through line (201) so that about 95 volume percent of the inlet gas passes through scrubbers (203) (205) heat exchangers (207) (209) and into the contactors (211), (213), (215), (217), (219), (221) of trains 1-6. Within these contactors, hydrogen sulfide and water in the inlet gas are partially absorbed onto the molecular sieves and the hydrogen sulfide is partially reacted into COS so that the treated gas effluent from the contactors has a suitable hydrogen sulfide and COS content and has a sufficiently reduced water content (preferably, less than −70° C. dew point) so that the majority of the effluent is passed into the treated gas header (223). A sufficient amount of treated gas is diverted from each of trains 1-6 as a slip stream through a heat exchanger (225), (227) and a heating furnace (229), (231) to raise the temperature of the effluent gas to about 290° C. and provide a flow of gas capable of regeneration of a molecular sieve bed by flow counter to the adsorption flow through contactors (233), (235) for a period sufficient to regenerate the contactor bed.

The regeneration gas from the contactors of phase I and phase II is collected in regeneration gas header (234) passed through a cooler (235) where the gas is cooled sufficiently to condense hydrocarbons and water which are removed from collector (237). The regeneration gas is then passed through a compression means (239) in which the pressure is raised to a range that is less than the pressure of the inlet gas. The compressed regeneration gas stream is then united with the remaining about 5 volume percent of inlet natural gas from inlet header (201) which has been heated in a heat exchanger (241) to a temperature equivalent to that of the regeneration gas. The combining of the gas streams is used to dilute the hydrogen sulfide content of the regeneration gas stream so that a diluted, regeneration gas stream is passed through scrubber (243) for further removal of condensables and water and through regeneration gas header (245) to the molecular sieve adsorbers of train 7. Train 7 which is a phase II operation for adsorbing regeneration gas impurities is operated like the trains of phase I with passage of the inlet gas through a scrubber (247), a heater (249) with a division of the flow between the adsorbers (251), (253), (255). The effluent from the adsorbers is of sufficiently low $H_2S$ and water content to be passed into the treated gas header (223) as salable gas where it is mixed with the effluent from the phase I adsorbers. A portion of the effluent sufficient in amount to regenerate a molecular sieve bed of train 7 is passed through heater (257) and furnace (259) to provide regeneration flow by back flow through an adsorber (261) of train 7 from which the effluent regeneration gas is passed to low pressure regeneration gas header (234) where it is admixed with the regeneration gas from the trains of phase I.

In this embodiment of the invention, the regeneration cycle of both phase I and phase II trains can be carried out in a cycle in which three of the four contactors in a train are in adsorption service while the fourth adsorber is being regenerated. In full operation, this allows, for instance, for a cycle of 36 hours of adsorption followed by 12 hours of regeneration, with the regeneration process moving seriatim through the four adsorbers in the train so that in a 48 hour period each of the adsorbers will have benefited from a 12 hour period of regeneration.

Figure 4:
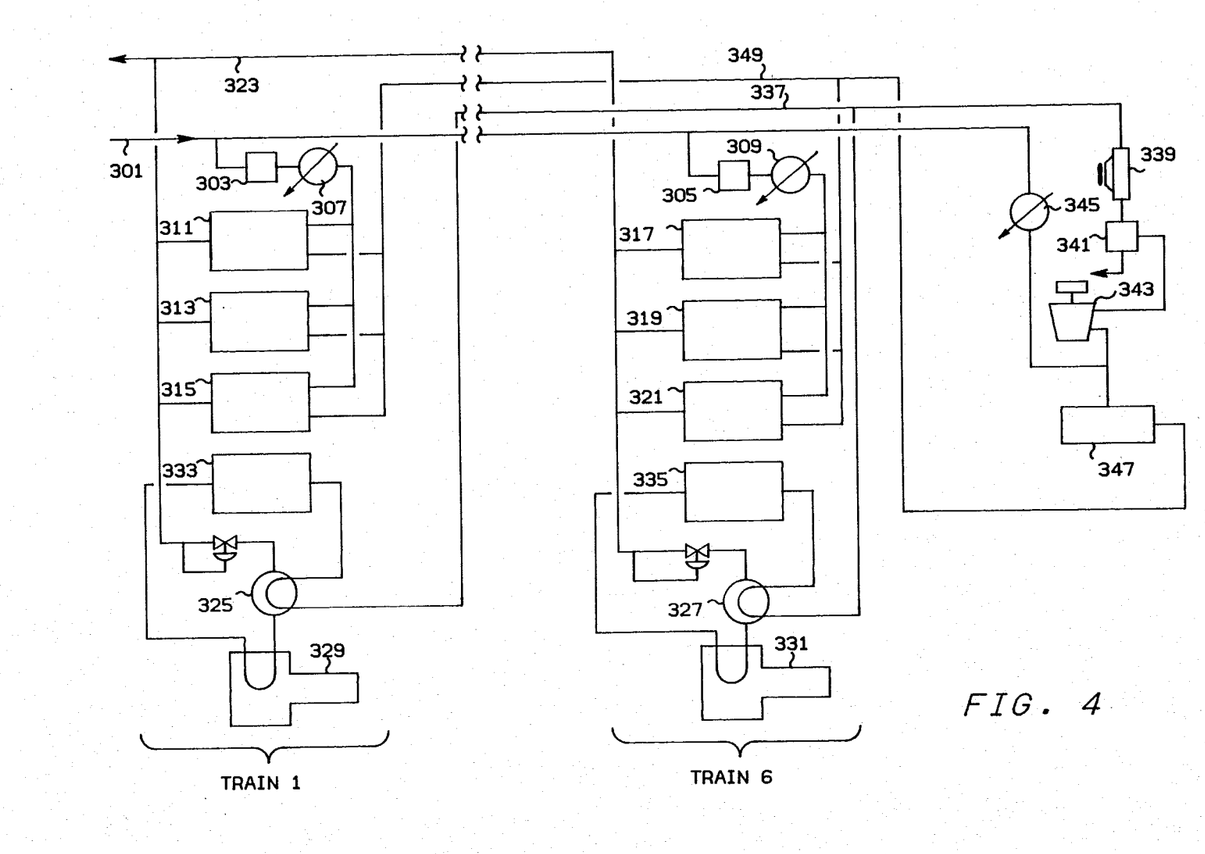
FIG. 4 shows a typical operating configuration of molecular sieve beds for the process of this invention using a single phase of adsorption and compression.

Referring now to FIG. 4, a process will be described in which low pressure regeneration gas is compressed to a pressure equal to the inlet pressure of the natural gas and all trains in service can be operated in the same manner without having two separate phases of adsorption. In this embodiment, natural gas entering through the inlet line (301) is divided equally among the trains. Here the trains are shown as 1-6, again showing only the pertinent lines of flow omitting the outer service lines which appear in a typical adsorption train as shown in FIG. 1. About 92 to about 95 volume percent of the inlet gas passes through a scrubber (303), (305) and a heater (307), (309) and is equally divided among the molecular sieve contactors (311), (313), (315), (317), (319), (321) in which the hydrogen sulfide and water in the inlet gas is partially adsorbed onto the molecular sieves and the hydrogen sulfide is partially reacted into COS so that the treated gas effluent from the contactors has a sufficiently low hydrogen sulfide content and water content to be passed to treated gas header (323) as salable material.

A sufficient portion of the treated gas in each of the trains is passed through a heater (325), (327), and a furnace (329), (331) by which the temperature of the gas is sufficiently raised to serve as regeneration gas for a contactor (333), (335) to regenerate the molecular sieves in the contactor and produce a low pressure regeneration gas which is transferred by header (337) to a cooler (339) where heavy liquids and water are condensed from the gas and removed from vessel (341). The low pressure regeneration gas is then passed through compression means (343) to raise the pressure to the same pressure as the inlet gas in header (301).

About 5 to about 8 volume percent of the inlet gas is passed through a heater (345) and admixed with the compressed regeneration gas to form a diluted regeneration gas stream. This stream is passed through a scrubber (347) for further removal of heavy hydrocarbons and water and through regeneration gas header (349) back to the adsorber trains where it is equally divided among the operating contactors (311), (313), (315), (317), (319), (321) so that each contactor has as inlet a mixed stream of inlet natural gas from header (301) and diluted regeneration gas from header (349). In full flow, continuous operation, it can be seen that the effluent from each of the operation adsorption contactors should be of approximately the same composition as far as remaining impurities and that the regeneration gas passing through the regenerating contactor in each train should have approximately the same composition.

A typical cycle operation for this embodiment of the invention allows each of the trains to be operated in the same manner so that, for example, in a 48 hour period each of the contactors will be in adsorption service for 36 hours with a seriatim 12 hour regeneration of the adsorbers.

It is readily apparent that in the various embodiments of this invention, using an adsorber system containing 4 A molecular sieves, hydrogen sulfide and water can be efficiently removed from a natural gas inlet stream to produce a salable product without complete dependence upon expensive amine and glycol adsorber systems. A two phase use of the adsorber system allows operation without using energy for compression. As the low pressure regeneration gas is subjected to compression, there is a trade off between use of energy and the flexibility of operating the system without devoting equipment to a second phase adsorption operation. The invention, therefore, offers alternative, economical processes for removing contaminants from a natural gas stream.

We claim:

1. An integrated process for removal of hydrogen sulfide and water from natural gas comprising passing an inlet natural gas stream containing hydrogen sulfide, $CO_2$, and water into contact with molecular sieves which act both as (1) an adsorbant for hydrogen sulfide and water and (2) catalyst in the reaction for conversion of hydrogen sulfide and carbon dioxide to carbonyl sulfide with, (a) treating of about 92 to about 95 volume percent of said natural gas stream by passing a first portion of said natural gas stream into contact with molecular sieves in a first phase contactors to produce, by adsorption and conversion of $H_2S$ to COS, a first treated gas stream of sufficiently low $H_2S$ and $H_2O$ content to be salable;

(b) passing a portion of this treated gas stream back through said molecular sieve beds of said first phase as regeneration gas to desorb the adsorbed $H_2S$ thereby producing a first low pressure regeneration gas stream;

(c) passing a second portion of said about 92 to about 95 volume percent of the natural gas inlet stream into contact with molecular sieves in a second phase of contactors to produce a second treated gas stream by adsorption and the reaction to form COS;

(d) passing said second treated gas stream through the molecular sieves of said second phase as regeneration gas thereby producing a second low pressure regeneration gas;

(e) uniting the low pressure regeneration gas streams of (b) and (d) and condensing heavy liquid hydrocarbons from the united low pressure regeneration gas streams; p1 (f) combining the united low pressure regeneration gas stream with the remaining about 5 to about 8 percent by volume of the inlet gas and subjecting this combined stream to scrubbing;

(g) contacting this combined stream with molecular sieves in the second phase of contactors thereby producing by adsorption and reaction of $H_2S$ to COS, a second treated gas stream of sufficiently low $H_2S$ and $H_2O$ content to be mixed with the first treated gas stream of (a) and retain salable quality; and (h) combining the effulent streams of (a) and (g)

2. A process of claim 1 wherein said molecular sieves are type 4 A molecular sieves.

3. An integrated process for removal of hydrogen sulfide and water from natural gas comprising passing an inlet natural gas stream containing hydrogen sulfide, $CO_2$, and water into contact with molecular sieves which act both as (1) an absorbent for hydrogen sulfide and water and (2) catalyst in the reaction from conversion of hydrogen sulfide and carbon dioxide to carbonyl sulfide with (a) passing about 92 to about 95 volume percent of said natural gas stream into contact with molecular sieves in a first phase of contactors to produce, by adsorption and conversion of $H_2S$ to COS, a first treated gas stream of sufficiently low $H_2S$ and $H_2O$ content to be salable;

(b) passing a portion of this first treated gas stream back through said molecular sieve beds of said first phase as regeneration gas to desorb the adsorbed $H_2S$ thereby producing a first low pressure regeneraion gas stream;

(c) combining said first low pressure regeneration gas and a second low pressure regeneration gas produced in step (g) below to form a united low pressure regeneration gas stream and condensing heavy liquid hydrocarbons and water from the united low pressure regeneration gas stream;

(d) subjecting said united low pressure regeneration gas stream to compression to produce a compressed gas stream having pressure at a level less than the pressure of the inlet gas;

(e) combining the compressed gas stream with the remaining about 5 to about 8 percent by volume of the inlet gas, subjecting the combined stream to scrubbing, (f) contacting this combined stream with molecular sieves in the second phase of contactors thereby producing by adsorption and reaction of $H_2S$ to COS a second treated gas stream of $H_2S$ content equally low as compared to the first phase of contactors but with a comparatively increased COS content;

(g) passing a portion of said second treated gas stream back through the molecular sieves of said second phase as regeneration gas thereby producing a second low pressure regeneration gas, and, (h) combining the first treated gas stream of (a) and the second treated gas stream of (f).

4. A process of claim 3 wherein said molecular sieves are type 4 A molecular sieves.

5. An integrated process for removal of hydrogen sulfide and water from natural gas comprising passing an inlet natural gas stream containing hydrogen sulfide, CO2, and water in to contact with molecular sieves which act both as (1) an absorbent for hydrogen sulfide and water and (2) catalyst in the reaction from conversion of hydrogen sulfide and carbon dioxide to carbonyl sulfide with (a) passing about 92 to about 95 volume percent of said natural gas stream into contact with molecular sieves in a first phase of contactors to produce, by adsorption and conversion of $H_2S$ to COS, a first treated gas stream of sufficiently low $H_2S$ and $H_2O$ content to be salable;

(b) passing a portion of this first treated gas stream back through said molecular sieve beds of said first phase as regeneration gas to desorb the adsorbed $H_2S$ thereby producing a first low pressure regeneration gas stream;

(c) condensing heavy liquid hydrocarbons and water from said first low pressure regeneration and gas stream;

(d) subjecting the effluent gas stream of (c) to compression to produce a compressed gas stream having pressure equal the pressure of the inlet gas;

(e) combining said compressed gas stream with the remaining about 5 to about 8 percent by volume of inlet gas to produce a combined gas stream;

(f) subjecting said combined gas stream to scrubbing to produce a scrubbed combined gas stream;

(g) mixing said scrubbed combined gas stream with the about 92 to about 95 percent by volume of inlet gas in step (a) for contact with molecular sieves; and, (h) passing said stream of (g) into contact with molecular sieves to produce by adsorbtion and conversion of $H_2S$ to COS a treated gas stream of sufficiently low $H_2S$ and $H_2O$ content to be salable.

6. A process of claim 5 wherein said molecular sieves are type 4 A molecular sieves.

* * * * *